United States Patent
Jones

(10) Patent No.: US 6,604,945 B1
(45) Date of Patent: *Aug. 12, 2003

(54) METHOD AND APPARATUS FOR IMPLANTATION

(76) Inventor: Shedrick D. Jones, 4330 Olympiad Dr., Los Angeles, CA (US) 90043

( * ) Notice: Subject to any disclaimer, the term of this patent is extended or adjusted under 35 U.S.C. 154(b) by 0 days.

This patent is subject to a terminal disclaimer.

(21) Appl. No.: 08/702,948

(22) Filed: Aug. 26, 1996

Related U.S. Application Data

(63) Continuation-in-part of application No. 08/614,494, filed on Mar. 13, 1996, now Pat. No. 6,135,772, which is a continuation of application No. 08/290,610, filed on Aug. 15, 1994, now abandoned.

(51) Int. Cl.⁷ .............................................. A61C 13/00
(52) U.S. Cl. ...................................... 433/173; 433/174
(58) Field of Search .............................. 433/173, 174, 433/175, 176, 201.1, 165, 221; 623/16; 606/65, 73; 411/420, 421

(56) References Cited

U.S. PATENT DOCUMENTS

| | | | | |
|---|---|---|---|---|
| 3,590,485 A | * | 7/1971 | Chereheve | 433/201.1 |
| 4,697,969 A | * | 10/1987 | Sparks | 411/421 |
| 4,713,004 A | * | 12/1987 | Linlow et al. | 433/174 |
| 4,872,840 A | * | 10/1989 | Bori | 433/173 |
| 5,076,788 A | * | 12/1991 | Niznick | 433/173 |
| 5,120,223 A | * | 6/1992 | Weissman | 433/215 |
| 5,194,000 A | * | 3/1993 | Dury | 433/173 |
| 5,205,745 A | * | 4/1993 | Kamiya et al. | 433/174 |
| 5,205,746 A | * | 4/1993 | Chanavaz | 433/174 |
| 5,269,686 A | * | 12/1993 | James | 433/174 |
| 5,312,256 A | * | 5/1994 | Scortecci | 433/174 |
| 5,316,477 A | * | 5/1994 | Calderon | 433/173 |
| 5,366,374 A | * | 11/1994 | Vlassis | 433/173 |
| 5,368,483 A | * | 11/1994 | Sutter et al. | 433/473 |

* cited by examiner

Primary Examiner—Cary E. O'Connor
(74) Attorney, Agent, or Firm—Robert E. Malm

(57) ABSTRACT

The invention is a method and apparatus for embedding an implant of a special design in bone tissue in a way that encourages bone tissue growth in and around the implant thereby achieving greater attachment security over longer periods of time. The user employs a bone-fragment collecting drill to form the bone-tissue hole and deliver the resulting bone fragments to a collecting region. The user crumbles the bone fragments by placing them in the lower of two mating spoon-shaped jaws of a pliers-like device and repeatedly opening and closing the jaws until the bone fragments are crumbled. The surface of the implant is equipped with one or more embedded helical channels and through-holes to permit bone growth into the implant. The installation of the implant consists of partially filling the bone-tissue hole with bone crumbs, packing the helical channels and through-holes with bone crumbs, and installing the implant in the bone-tissue hole. The interspace between the implant and the bone tissue becomes filled with the patient's own bone tissue during the installation process thereby greatly encouraging the growth of bone tissue in and around the implant.

5 Claims, 3 Drawing Sheets

METHOD AND APPARATUS FOR IMPLANTATION

CROSS-REFERENCES TO RELATED APPLICATIONS

This is a continuation-in-part of Application Ser. No. 08/614,494, filed Mar. 13, 1996, now U.S. Pat. No. 6,135,772, which in turn is a continuation of Application Ser. No. 08/290,610, filed Aug. 15, 1994, now abandoned.

BACKGROUND OF THE INVENTION

This invention relates generally to dental and skeletal implants for attaching prosthetic devices to bone tissue.

There are two requirements for achieving a secure and long-lasting implant embedded in bone tissue. The implant must be mechanically strong in order to resist the stresses to which it is subjected and it must be biologically compatible with the bone tissue in order that it may encourage bone growth around it.

Implants made of metal are attractive from the mechanical strength aspect but except for a few exceptions such as pure titanium and the titanium alloy Ti 6Al 4V, most are biologically undesirable in that they release metal ions which are harmful to living tissue. Implants made of ceramics such as single-crystal alumina do not release harmful ions and are mechanically strong but do not bond well to living tissue. Biologically-compatible ceramics such as apatite, which bond well to living tissue, lack the mechanical strength required of implants.

Because of its mechanical strength and its ease of fabrication, metal remains the material of choice for most implants. In order to enhance the growth of living bone tissue, the metal implants are coated with biologically-compatible materials. In order to minimize the inadequacies of biological bonding, the implants are often screwed into the bone tissue thereby seeking to achieve by mechanical means what can't quite be achieved by means of biological bonding. In order to maximize the effects of bone growth to the greatest degree possible, the implant is provided with holes, recesses, and other features into which bone growth may proceed, hopefully thereby preventing the implant from loosening over time.

Unfortunately, the bone tissue often does not grow back into the interspaces between the implant and the bone tissue where it is lodged. Instead, soft tissue grows in these regions. This soft tissue contributes little to the strength of attachment between implant and the adjacent bone tissue.

SUMMARY OF THE INVENTION

The present invention is a method and apparatus for embedding an implant of a special design in a way that encourages bone tissue growth in and around the implant thereby achieving greater attachment security over longer periods of time. The method comprises the steps of forming a hole in the bone tissue at the desired site of the implant, collecting the bone fragments that result from forming the hole, crumbling the bone fragments, packing the crumbled bone fragments in the hole and in and around the implant, and installing the implant in the hole.

The method steps of forming the hole in the bone structure and collecting the bone fragments are performed with a bone-fragment collecting drill comprising a coaxial assembly of a tubular saw and a drill, the tubular saw and drill acting in concert to form the hole and deliver the resulting bone fragments to an enclosed region between the tubular saw and the drill.

The crumbling step is performed with a hand-operated crumbling device comprising a pliers-like assembly wherein the jaws are spoon shaped, the convex surface of one jaw mating with the concave surface of the other jaw when the jaws are closed. The user performs the crumbling step by placing the bone fragments in the concave lower jaw and repeatedly opening and closing the jaws to accomplish the crumbling function. The crumbled bone fragments are either retained within the spoon-shaped lower jaw or, alternatively, sieved through small openings in the lower jaw.

The implant comprises a main portion and a terminal portion. The main portion has one or more helical channels embedded in the surface of the implant for the purpose of transporting crumbled bone fragments that are placed in the bone-tissue hole prior to the installation of the implant. Transverse through holes are provided at various levels along the implant longitudinal axis to permit bone tissue growth into the implant.

The method step of packing consists of partially filling the hole with crumbled bone fragments and also packing the implant channels and holes with crumbled bone fragments.

The method step of installing the implant consists of installing the implant in the hole. Interface regions between the implant and the bone tissue become filled with the patient's own bone tissue during the installation process thereby greatly encouraging the further growth of bone tissue in and around the implant.

DESCRIPTION OF THE PREFERRED EMBODIMENTS

This invention consists of a bone-fragment collecting drill for making a hole in bone tissue and collecting the bone fragments that result from the activity, a bone-fragment crumbling device, an implant designed to distribute bone-fragment crumbs placed in the hole to the interspaces between implant and hole, and a method for using these devices to achieve a secure and long-lasting attachment means for dental and skeletal prosthetic devices.

Figure 1:
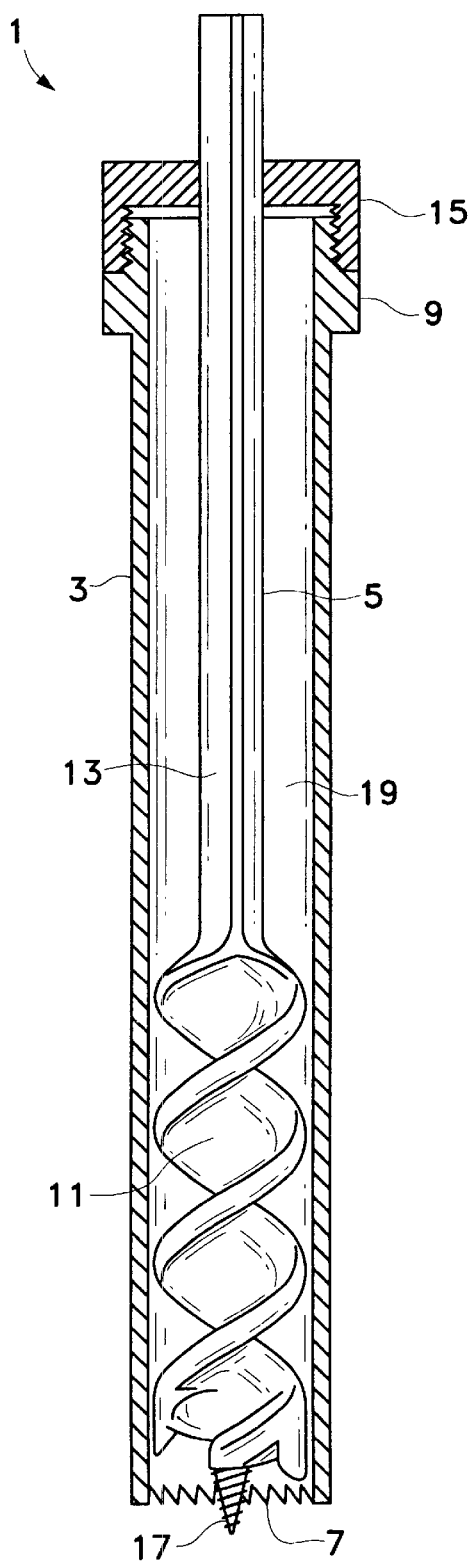
FIG. 1 is a side view of the collecting drill.

The bone-fragment collecting drill 1 is shown in FIG. 1. It consists of the coaxial assembly of the tubular saw 3 and the drill 5. The tubular saw 3, shown in FIG. 1 in cross section, is a thin-walled stainless-steel cylinder having a plurality of saw teeth 7 along the edge of the cylinder wall at the distal end and a screw-type connecting means 9 at the proximal end.

The drill 5 consists of a fluted section 11 at the distal end and a shaft 13 at the proximal end. The fluted section 11 terminates in a pointed member 17 which guides the bone-fragment collecting drill 1 during the hole-drilling operation. A screw-type connector 15, designed to mate with the screw-type connector 9 of the tubular saw 3, is fastened to the shaft 13 at the proximal end.

When the tubular saw 3 and the drill 5 are assembled as shown in FIG. 1, the pointed member 17 extends beyond the distal end of the tubular saw 3 so that the pointed member 17 makes contact with bone tissue before the saw teeth 7 when drilling is initiated. The diameter of the fluted section 11 is slightly smaller than the inside diameter of the tubular saw 3 to allow easy assembly.

The connecting means 9 and 15 are hexagonal in shape to permit wrenches to be applied in disassembling the tubular saw 3 and the drill 5. The end of the shaft 13 that projects from the connecting means 15 can be used for connecting to a power source for the purpose of driving the bone-fragment collecting drill 1. The shaft 13 could also be terminated at the connecting means 15, in which case the power source would be attached to the connecting means 15.

In operation, bone fragments and debris resulting from the cutting operations of the tubular saw 3 and the drill 5 are transported by the flutes of the fluted section 11 to the region 19 between the tubular saw 3 and the shaft 13. At the conclusion of the drilling operation, the bone-fragment collecting drill can be disassembled and the bone fragments recovered.

Figure 2:
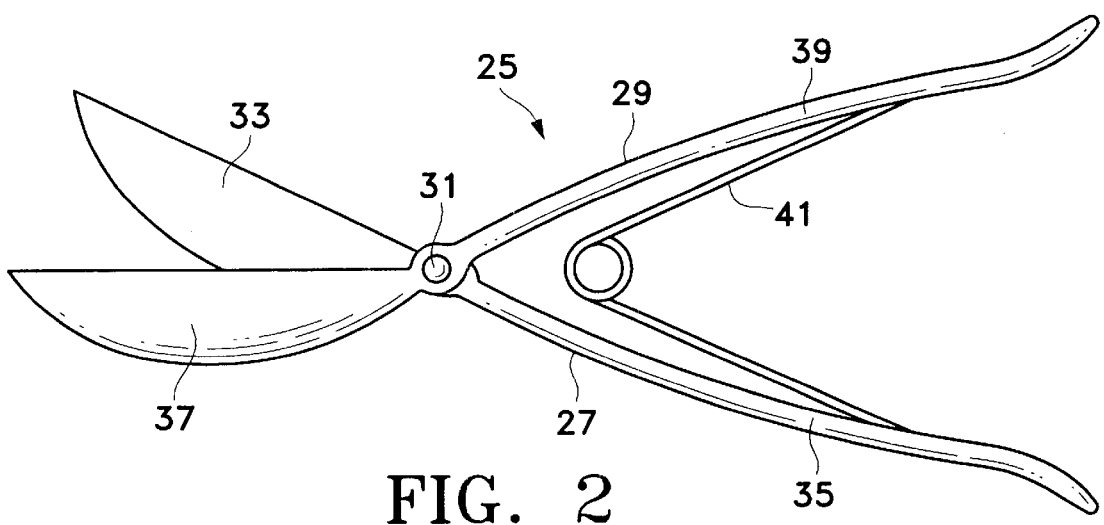
FIG. 2 is a side view of the bone-fragment crumbling device.

The bone fragments are crumbled by the hand-operated crumbling device 25 shown in FIG. 2. The device consists of the crumbling member 27 and the opposing member 29 that pivot in opposite directions about the pin 31 during operation. The device is preferably made of a material such as pure titanium or the titanium alloy Ti 6Al 4V which are non-corrodible, readily sterilizable, and have the requisite strength for crumbling bone fragments.

Figure 3:
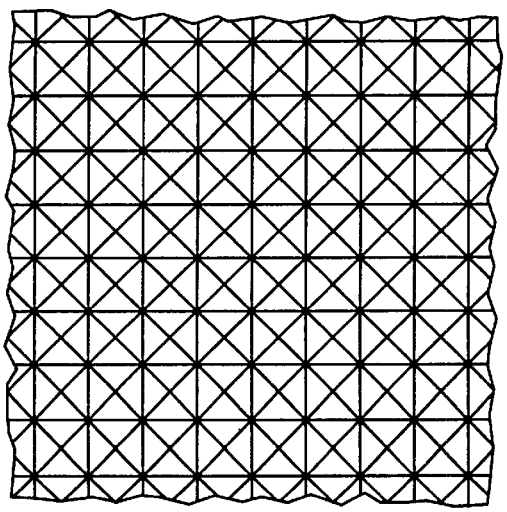
FIG. 3 is a magnified view of a portion of the convex side of the crumbling jaw of the bone-fragment crumbling device.

The crumbling member 27 consists of the spoon-shaped crumbling jaw 33 and the crumbling lever arm 35. A small portion of the convex surface of the crumbling jaw 33 is illustrated in FIG. 3. It is comprised of a grid of pyramids with bases that are roughly 2 mm square and heights that are roughly 2 mm.

Figure 4:
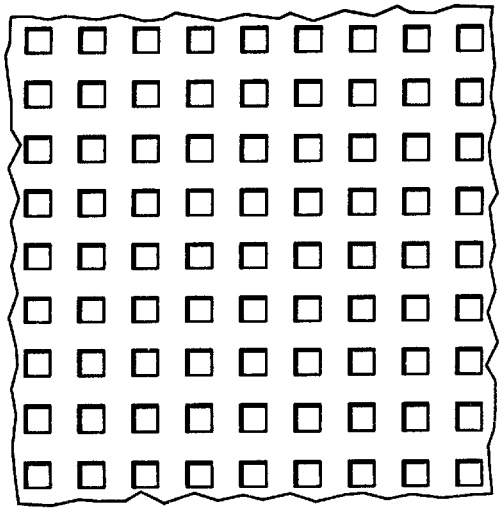
FIG. 4 is a magnified view of a portion of the opposing jaw of the bone fragment crumbling device.

The opposing member 29 consists of a spoon-shaped opposing jaw 37 that conforms to the crumbling jaw 33 when the two jaws come together and the opposing lever arm 39. A small portion of the surface of the opposing jaw 37 is illustrated in FIG. 4. It is comprised of a grid of square openings that are roughly 1 mm square.

The jaws 33 and 37 are normally held open by the spring 41 which exerts opposing forces on lever arms 35 and 39 tending to spread them apart. The crumbling device is operated by the user gripping the lever arms 35 and 39 with one hand, forcing the lever arms together, and then releasing them so that they can return to their normal open positions. This operation, repeatedly performed, causes bone fragments placed in the opposing jaw 37 to be crumbled, and results in bone-fragment crumbs smaller than the openings in opposing jaw 37 to pass through the openings and be collected in a container beneath the jaw.

There are a variety of suitable alternative designs for the crumbling jaw 33. The essential requirement is that the surface that comes in contact with the bone fragments be rough comprising a plurality of peaks and valleys. The peaks should be sharp so as to penetrate the bone fragments and the larger crumbs and cause them to split into smaller pieces. The spacing of the peaks should be comparable to the largest permissible crumb size.

There are also a variety of suitable alternative designs for the opposing jaw 37. The opposing jaw can be without openings thereby retaining all crumbs, regardless of size, within the jaw. If it is desirable not only to crumble the bone fragments but also to separate the larger crumbs from the smaller crumbs, then the opposing jaw can be designed with openings of an appropriate size. The openings can be square, round, or of any other shape that can perform the separation function.

Figure 5:
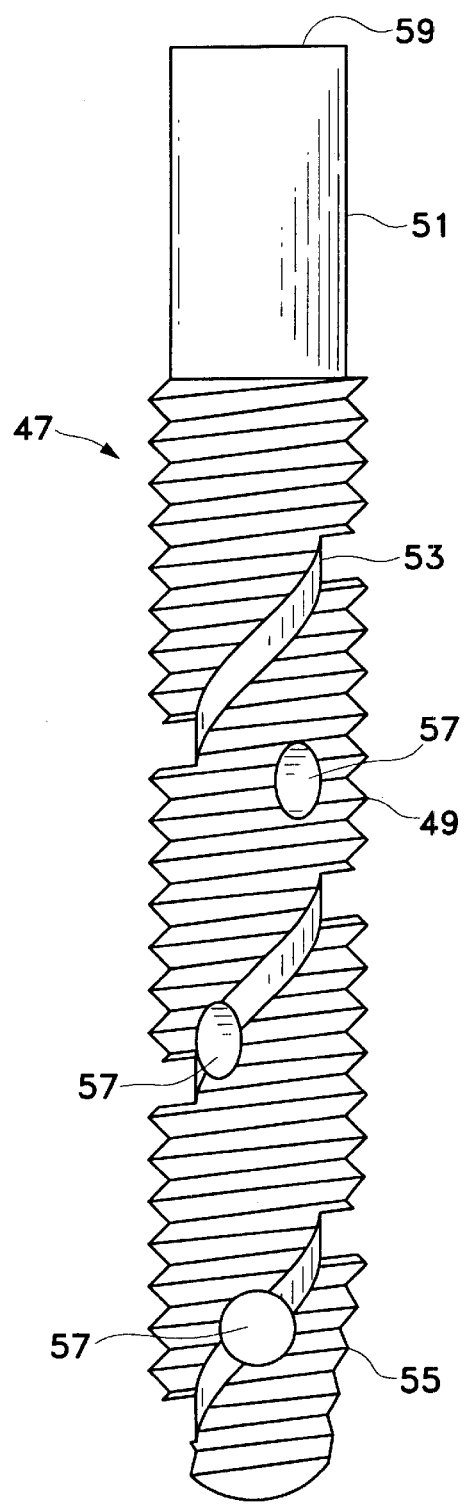
FIG. 5 is a side view of the first embodiment of the implant.
Figure 6:
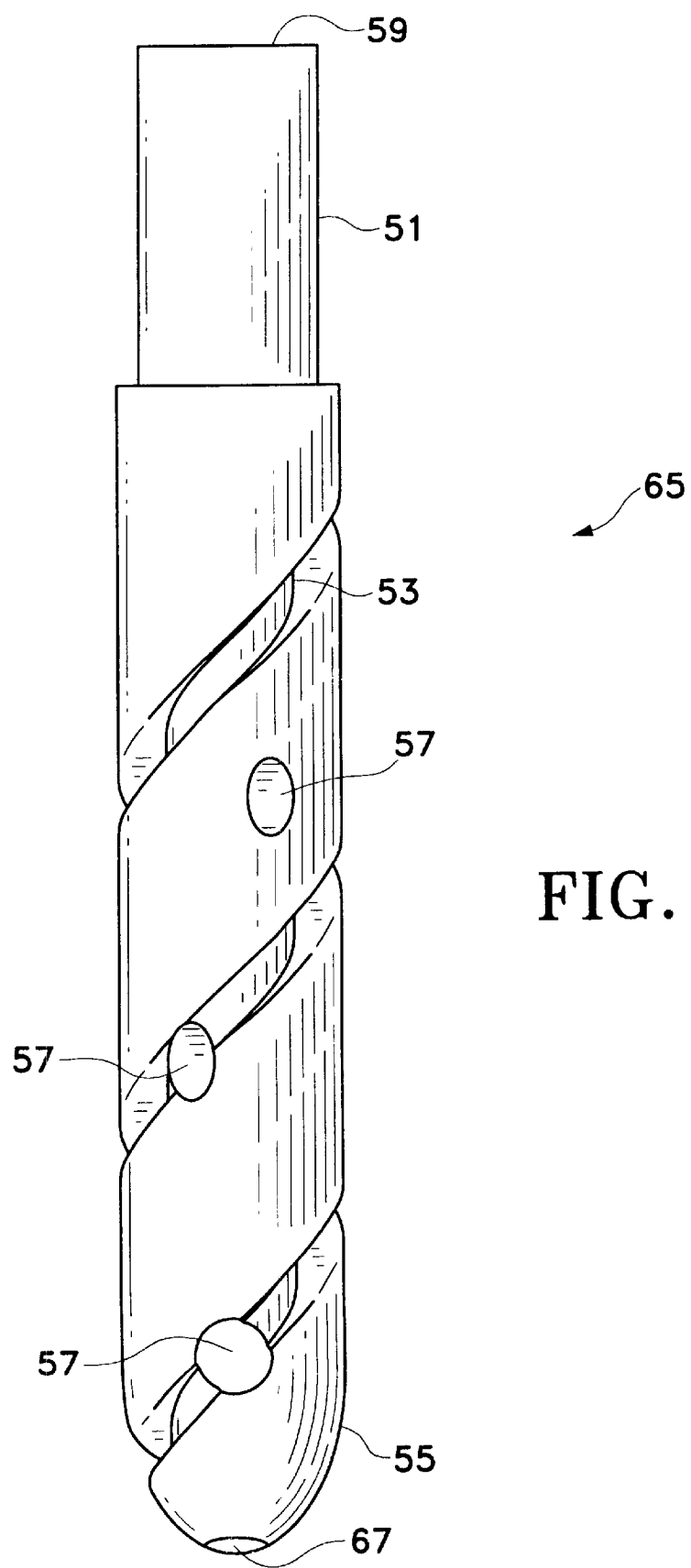
FIG. 6 is a side view of a second embodiment of the implant.

Side views of the crumb-distributing implants 47 and 65 are shown in FIGS. 5 and 6 respectively. The implant 47 shown in FIG. 5 is a solid cylinder with-screw threads 49 extending from the distal end to the terminal portion 51 of the implant. The terminal portion 51 provides the means for attaching a prosthesis. The implant 65 shown in FIG. 6 is similar in all respects to implant 47 except that it does not have the screw threads 49 and has in addition the coaxial hole 67 which connects to hole 57.

At least one helical channel 53 is embedded in the surface of the implant throughout the threaded portion. The intersection of the helical channel with the threads results in the threads having cutting edges which permit the implant to cut its own threads in bone tissue when it is installed. To facilitate the thread-cutting process, the threaded portion has a tapered section 55 at the distal end to allow easy entry into the hole in the bone tissue.

The primary purpose of the helical channel 53 is to carry bone-fragment crumbs deposited in the bone-tissue hole prior to installation of implant 47 or implant 65 away from the distal end and distribute them throughout the threaded portion of the implant. The helical channel 53 also provides a place for packing bone-fragment crumbs prior to installation of the implant.

The threaded portion of the implant 47 and the corresponding portion of implant 65 also include diametrical holes 57 in the implant at various levels along the axis of the implant and connecting to the helical channel 53. The diametrical holes 57 may optionally pass all the way through the implant.

The purpose of the holes is to provide receptacles for packing crumbled bone tissue prior to installation of the implant and avenues for bone tissue growth after installation.

A hexagonal recess is provided in the proximal end 59 of implants 47 and 65 by means of which a user can engage the implant with a hexagonal driving tool for the purpose of screwing the implant into a receiving hole in bone tissue in the case of implant 47 or rotating the implant back and forth while pressing the implant into a hole in soft bone in the case of implant 65. The proximal end 59 may also include a tapped hole below the hexagonal recess for the purpose of attaching a prosthesis to the implant. The terminal end 51 can be tapered to assure that the attachment of the prosthesis is accomplished in a secure manner. Other types of driving-tool-engaging means and other types of prosthesis-attachment means can also be used.

Implants 47 and 65 are made of a biocompatible material such as pure titanium or a titanium alloy exemplified by Ti 6Al 4V. To encourage bone tissue growth in and around the implant, the implant may be coated or plasma-sprayed with hydroxyapatite. For dental applications, the diameter of the implant is typically in the range from 3 to 4 mm with lengths ranging from 6 to 16 mm. The diameter of a femoral implant typically ranges from 6 mm to 16 mm with lengths ranging from 140 to 190 mm.

What is claimed is:

1. Implant apparatus comprising:
   a collecting device for making a bone-tissue hole in bone tissue and converting the bone tissue that was resident in the hole into bone fragments, the collecting device also collecting the bone fragments;

an implant device having a channel for receiving the bone fragments produced by the collecting device.

2. A method for using the implant apparatus of claim 1 comprising the steps:

making a bone-tissue hole in bone tissue and collecting the bone fragments using the collecting device;

impregnating the implant device with the bone fragments;

implanting the implant device in the bone-tissue hole.

3. The method of claim 2 further comprising the step:

placing a portion of the bone fragments in the bone-tissue hole prior to implanting the implant device in the hole.

4. A method for providing a means for attaching a prosthesis to bone tissue comprising the steps:

simultaneously making a hole in bone tissue, converting the bone tissue that was resident in the hole into bone fragments, and collecting the bone fragments;

providing an implant to which the prosthesis can be attached and which can be impregnated with the bone fragments;

impregnating the implant with the bone fragments;

installing the impregnated implant in the bone-tissue hole.

5. A method for implanting in bone tissue an implant device that provides support for a prosthesis, the implant device being a cylinder comprising a main section and a terminal section, the main section having at least one helical channel embedded in its surface, the method comprising the steps:

making a hole in bone tissue, converting the bone tissue that was resident in the hole into bone fragments, and collecting the bone fragments;

impregnating the implant device with the bone fragments;

installing the impregnated implant device in the bone-tissue hole.

* * * * *